United States Patent [19]
Crenshaw et al.

[11] Patent Number: 5,151,448
[45] Date of Patent: Sep. 29, 1992

[54] METHOD FOR TREATING PREMATURE EJACULATION

[76] Inventors: Roger T. Crenshaw, Ste. 2132; Mark G. Wiesner, Ste. 2131, both of 8950 Villa La Jolla, La Jolla, Calif. 92037

[21] Appl. No.: 729,221

[22] Filed: Jul. 12, 1991

[51] Int. Cl.⁵ .......................................... A61K 31/135
[52] U.S. Cl. .................................................... 514/651
[58] Field of Search ....................................... 514/651

[56] References Cited

U.S. PATENT DOCUMENTS 4,194,009  3/1980  Molloy et al. ................. 564/347 X
4,647,591  3/1987  Cherkin et al. ..................... 514/651

OTHER PUBLICATIONS

Avery's Drug Treatment, Third Ed., 1987, pp. 1178-1179.

*Primary Examiner*—Leonard Schenkman
*Attorney, Agent, or Firm*—Dressler, Goldsmith, Shore, Sutker & Milnamow, Ltd.

[57] ABSTRACT

Premature ejaculation by a male human patient is treated by administration of fluoxetine.

7 Claims, No Drawings

METHOD FOR TREATING PREMATURE EJACULATION

TECHNICAL FIELD

This invention relates to the treatment of a sexual dysfunction. More particularly, this invention relates to the treatment of premature ejaculation in a human male patient.

BACKGROUND OF THE INVENTION

Premature ejaculation is a sexual dysfunction that has been variously estimated to effect up to 75 percent of the population (Kinsey et al., 1949, p. 580; Masters and Johnson 1967, 1971 and 1973). Regardless of the figures in the literature and the definition of premature ejaculation, this problem has remained substantially unchanged in the past twenty years regardless of the psychological, biochemical, pharmacological and clinical psychiatric literature. The term "premature ejaculation" includes congenital premature ejaculation as well as primary premature ejaculation where the male ejaculates extremely rapidly, e.g., prior to penetration with coitus or within ten to twenty strokes after intromission, so as to adversely affect the sexual relationship between the involved partners. The psychoanalytical definition of ejaculation, in less than one minute, also suffices for these purposes as well as the Masters and Johnson definition where the male ejaculates 50 percent of the time more rapidly than the female is able to have an orgasm if she has no orgasmic dysfunction of her own. Premature ejaculation by any of the foregoing definitions can be treated by the method of the invention.

Premature ejaculation is a considerable factor in sexual as well as marital discord. It is estimated that this factor is present in at least about 20 percent of clinical cases. However, heretofore an effective, relatively inexpensive treatment that can be administered by any practicing physician without specialized knowledge has not been available.

SUMMARY OF THE INVENTION

Premature ejaculation in male human patients can be effectively treated by the administration, preferably oral, of a fluoxetine dose effective to delay the onset of ejaculation during subsequent sexual intercourse. One preferred mode of treatment within the purview of the present invention is the chronic administration of fluoxetine in an amount in the range of about 5 milligrams to about 80 milligrams per day.

Oral administration is the preferred route of administration. Fluoxetine is preferably administered as the hydrochloride salt, i.e., as fluoxetine hydrochloride.

DETAILED DESCRIPTION OF PREFERRED EMBODIMENT

Fluoxetine is a known antidepressant and is commercially available under the trade designation Prozac ® as fluoxetine hydrochloride. This compound can be represented by the formula

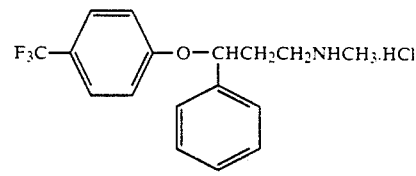

and is also known by its chemical name as (±)-N-methyl-3-phenyl-3-[(λ,λ,λ-trifluoro-p-tolyl)-oxy]propylamine hydrochloride. The molecular weight of fluoxetine hydrochloride is 345.79. It is a white to off-white crystalline solid and exhibits a solubility in water of about 14 milligrams per milliliter.

The synthesis of fluoxetine and of the acid addition salts thereof is described, inter alia, in U.S. Pat. No. 4,194,009 to Molloy et al.

It has now been found that premature ejaculation in a male human patient suffering from such an affliction can be effectively ameliorated and treated by the administration to the patient of an effective dose of fluoxetine either in its free base form or its acid addition salt form. Fluoxetine is an amine, and, as is well known, amines readily form acid addition salts with inorganic acids as well as organic acids.

The term "fluoxetine," as used herein and in the appended claims, means the free base form as well as an acid addition salt form of (±)-N-methyl-3-phenyl-3-[(α,α,α-trifluoro-p-tolyl)-oxy]propylamine. Also included within the purview of this invention is the use of the pharmacologically acceptable salts of the fluoxetine base formed with substantially non-toxic acids. Such acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylates, phenyl-substituted alkanoates, hydroxy alkanoates and alkanedioates, aromatic acids, aliphatic and aromatic sulfonic acids, etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonates, naphthalene-1-sulfonate, naphthalene-2-sulfonate, mandelate and the like salts. While fluoxetine is an anti-anxiety drug, it is to be noted that other anti-anxiety drugs such as chlordiazepoxide (Librium ®) and diazepam (Valium ®) are not suitable for the treatment of premature ejaculation.

For the treatment contemplated by the present invention, the preferred route of administration is oral administration; however, other routes of administration, e.g., parenteral, by suppositories, buccal dosage forms, skin patch, and the like, can also be utilized. The active ingredient in the individual dosage forms can be combined with the conventional pharmaceutical excipients and formed into tablets, capsules, and the like. Tablets may be scored for divided dosage administration. Alternatively, the active ingredient may be dissolved in a suitable liquid vehicle such as water, fruit juice, or the like. For chronic administration of the active ingredient oral dosage forms are preferred.

The specific dosage and duration of treatment may vary depending upon the particular patient. However, usually premature ejaculation is successfully treated by administering fluoxetine in a daily dose in the range of about 5 milligrams to about 80 milligrams for a time period of at least about 3 months, preferably for a time period of at least about 6 months. In some instances fluoxetine is administered chronically as long as the patient remains sexually active. A daily dose of about 20 milligrams is preferred The administered dosage can also vary over a period of time. A particularly preferred such treatment regimen contemplates the administration of a daily dose of about 20 milligrams for the first two weeks of treatment, then a daily dose of about 40 milligrams for the next four weeks of treatment, next a daily dose of about 20 milligrams for two weeks, followed by a daily maintenance dose of about 10 milligrams for an extended time period as required.

The present method of treatment provides at least three major areas of improvement over the old methods for control of premature ejaculation which mainly followed behavioral cognitive methodology and relied upon a model which was threefold: (1) that premature ejaculation was due to prior conditioning and therefore largely in part to the person's rapid masturbatory behavior as an adolescent, (2) that there was some anxiety involved and therefore a release of adrenaline to the neuroreceptors causing a flight/fight/fear mechanism and sympathetic activity increase of the nervous system and (3) that there was an increased muscular tone (increased beta afferent neurological response) which caused the person to ejaculate rapidly due to increased rapidity of all reflexes. In addition, there is fourth postulate that is (4) a difference biologically between males with premature ejaculation and those males without premature ejaculation, which may be borne out in some of the literature describing cortical evoked potentials. See, for example, Andrologia 20(4):326-330 (1988). Using any of these models for purposes of comparison, the present method accomplishes the following: (A) specialized information to treat the person with premature ejaculation is not required, (B) the treatment of premature ejaculation is achieved rapidly with medication available to all physicians.

In addition, the cost of treatment to the patient is reduced at least about six-fold. Such improvements in reduced cost, delivery, and access, as well as the fact that any licensed physician can prescribe this medication, provide a significant advantage over that what was heretofore available to the estimated 23 million male patients in the United States alone who suffer from premature ejaculation but many of whom may not have access to the limited number of qualified therapists.

The present invention is further illustrated by the following case studies.

Case 1

A 42-year old white male presented a lifetime history of premature ejaculation. He ejaculated within 10 to 20 seconds after arousal, either by manual or oral stimulation, and always ejaculated within two to three strokes of penetration. He and his wife arrived at therapy after seven years of marriage with extreme marital as well as sexual dysfunction. This male was treated for approximately three years with all standard methodology described in the medical literature to no avail, and at the end of three years was considered a therapeutic failure. Thereafter, this particular male was treated with Prozac ® according to the present invention. Within two months, at 20 mg./day for the first month and 40 mg./day for the second month, the male patient was able to have intromission with active thrusting for approximately two minutes. He and his wife now are capable of having sex on a frequent basis and often describe their lovemaking sessions as lasting over an hour. The male patient does not ejaculate prior to intromission.

Case 2

A 24-year old Chinese male presented a history of premature ejaculation. He generally ejaculated prior to insertion and usually with first touching of the penis by the female. Treatment with Prozac ® was begun on Day 1. By Day 15, he had obtained sufficient ejaculatory control to obtain intromission and could maintain active thrusting for over five minutes. The patient was continued on Prozac ® at the 20 mg. level. The treatment was continued for six months with no relapse.

Case 3

A 55-year old male presented some degree of intermittent episodic impotence and premature ejaculation for all of his life. He attributed his premature ejaculation to his three divorces. He always ejaculated in less than 30 seconds upon all sexual encounters with every female. Intromission with any active thrusting in the male astride position was always rapid. The patient was begun on Prozac ®, 20 mg./day, for the first month with minimal improvement. His dosage was increased to 40 mg./day for the second month and he was found to be able to obtain intromission with active thrusting in the male superior position for over five minutes. He was continued in follow-up for six months; thereafter Prozac ® was stopped. The patient did not return for follow-up and is presumed to have been cured.

Case 4

A 32-year old male presented a history of multiple failed relationships due to premature ejaculation. He reported that he always ejaculated within 10 to 20 seconds of intromission, that he was able to last only 10 strokes, and that he would make up for it with either oral sex or hand stimulation, but that most female partners felt "cheated." He was started on a 20 mg.-daily dose of Prozac ® on Day 1. On Week 2 his dosage was increased to 40 mg./day. At Week 6, the dosage was decreased from 40 mg./day back to 20 mg./day. At the end of Week 8, the patient was ejaculating with intromission only after five to ten minutes.

Case 5

The patient, a 41-year old white male, reported that he ejaculated in generally less than one minute, and that his wife was extremely unsatisfied with their lovemaking. The patient was started on Prozac ® on Day 1 at 20 mg./day, the dosage was increased to 40 mg./day on Day 14. Dosage was reduced to 20 mg./day due to anorgasmia on Day 30, decreased to 10 mg./day on Day 50, and decreased to 5 mg./day on Day 60. At the end of six months, this patient was essentially cured and removed from any further medication. A follow-up after four months revealed that the patient was still cured. No further therapy was deemed necessary at that time.

Case 6

A 56-year old white male presented a life-long history of premature ejaculation as well as a six year history of erective insecurity and intermittent episodic impotence. He was also in the process of urological evaluation. It was found that he had a decreased nocturnal penile tumescence as well as a decreased Doppler value of 0.7. His testosterone was within normal limits. The patient was begun on Prozac ® at a dose of 20 mg./day for the first month of treatment. Only minimal improvement was noted. Thereafter the daily dose was increased to 40 mg./day. Four weeks after Prozac ® was administered at 40 mg./day, an inflatable penile prosthesis of the Mentor type was inserted in the patient to correct his erective insecurity. The patient sill had premature ejaculation upon revisit, but had stopped taking Prozac ®. Since he was able to sustain the erection due to the implantation of the intrapenile prosthesis, he did not see any particular reason to prolong onset of his ejaculations.

Case 7

A 36-year old white male reported a ten year conflicted history of marital relationship. He had premature ejaculation; he ejaculated generally within 10 to 30 strokes of intromission, although he did not ejaculate quickly with either oral sex or hand stimulation by his wife. He appeared to use premature ejaculation to punish his wife for real or imagined transgressions in the relationship. He took Prozac ®, 20 mg./day, for three weeks, and appeared to be obtaining very excellent results in that onset of his ejaculations was now 3 to 4 minutes after intromission. Thereafter he began taking his medications only sporadically. Upon achieving a fair degree of success, he stopped all medications and refused further therapy, indicating a probable need for intervention in the marital dynamics rather than in the sexual dynamics of this relationship. The patient had no side effects from the medication and had no other reasons that he could elucidate for stopping the medication.

Case 8

A 36-year old white male reported a history of lifelong premature ejaculation. He ejaculated usually upon intromission or within 10 to 20 strokes. He had no history of relationships or marriages. His longest relationship, due to his sexual dysfunction, was approximately three months. He was begun on 20 mg. of Prozac ® per day. Since he tolerated the medication without difficulty, at the end of two weeks the dosage was increased to 40 mg. of Prozac ® per day. At the end of one month, he was able to last approximately 5 minutes with active coital penetration and thrusting in numerous positions. He was continued on 40 mg. of Prozac ® per day. At the present time he is at the fourth month of therapy.

The foregoing description and the accompanying case studies are presented as illustrative but are not to be construed as limiting the present invention. Still other variations within the spirit and scope of this invention are possible and will readily present themselves to those skilled in the art.

We claim:

1. A method of treating a male human patient suffering from premature ejaculation which comprises administering to the patient a dose of fluoxetine effective to delay the onset of ejaculation by the patient during subsequent sexual intercourse.

2. The method in accordance with claim 1 wherein fluoxetine is administered chronically and daily in an amount in the range of about 5 milligrams, to about 80 milligrams per day.

3. The method in accordance with claim 1 wherein fluoxetine is administered daily for a time period of at least about 3 months and in an amount in the range of about 5 milligrams to about 80 milligrams per day.

4. The method in accordance with claim 1 wherein fluoxetine is administered daily for a time period of at least about 6 months and in an amount in the range of about 5 milligrams to about 80 milligrams per day.

5. The method in accordance with claim 1 wherein fluoxetine is administered daily to the patient orally and as fluoxetine hydrochloride in a pharmacologically suitable carrier.

6. The method in accordance with claim 1 wherein fluoxetine is administered daily to the patient orally as fluoxetine hydrochloride and according to the following schedule: (1) first a daily dose of about 20 milligrams for a time period of about two weeks, (2) then a daily dose of about 40 milligrams for a time period of about four weeks, (3) next a daily dose of about 20 milligrams for a time period of about two weeks, and (4) thereafter a daily dose of about 10 milligrams as a maintenance dose.

7. The method in accordance with claim 1 wherein fluoxetine is administered as a fluoxetine hydrochloride solution in an aqueous medium.

* * * * *